United States Patent [19]

Adam et al.

[11] Patent Number: 4,593,040

[45] Date of Patent: Jun. 3, 1986

[54] COMPOSITIONS FOR COMBATTING PHYTOPATHOGENICAL FUNGI AND BACTERIA EMPLOYING MIXTURES OF BENZYL PHENOL DERIVATIVES AND CARBENDAZIN

[75] Inventors: Lothar Adam, Kleinmachnow; Ursula Albrecht, Wilhelmshorst; Ulrich Burth, Kleinmachnow; Axel Kramer, Greifswald; Sieghard Lück, Teltow; Rainer Müller, Kleinmachnow; Lothar Neeb, Berlin; Hubert Rattba, Teltow; Wolfgang Weuffen, Greifswald, all of German Democratic Rep.

[73] Assignee: VEB Berlin-Chemie, Berlin, German Democratic Rep.

[21] Appl. No.: 408,582

[22] Filed: Aug. 17, 1982

[30] Foreign Application Priority Data

Jun. 25, 1981 [DD] German Democratic Rep. ................... 2311483
Nov. 20, 1981 [DD] German Democratic Rep. ................... 2350192
Mar. 17, 1982 [DD] German Democratic Rep. ................... 2382263

[51] Int. Cl.$^4$ ................... A01N 31/08; A01N 43/52
[52] U.S. Cl. ................... 514/395; 514/736
[58] Field of Search ................... 424/273, 347; 514/395, 514/736

[56] References Cited

U.S. PATENT DOCUMENTS 3,631,175 12/1971 LaLiberte ................... 260/307
3,657,443 4/1972 Klopping ................... 424/273

FOREIGN PATENT DOCUMENTS 1237731 3/1967 Fed. Rep. of Germany .
1209799 3/1970 Fed. Rep. of Germany .
1745784 3/1972 Fed. Rep. of Germany .
110423 12/1974 Fed. Rep. of Germany .
78423 12/1970 German Democratic Rep. .
107204 7/1974 German Democratic Rep. .
131746 3/1976 German Democratic Rep. .
130427 3/1977 German Democratic Rep. .
1195180 6/1970 United Kingdom .

Primary Examiner—Allen J. Robinson
Attorney, Agent, or Firm—Jordan and Hamburg

[57] ABSTRACT

The invention relates to synergistically active mixtures for the control of phytopathogenic fungi and bacteria comprising antimicrobially effective derivatives of a phenol of the general formula

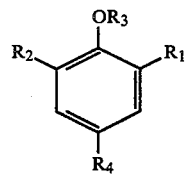

wherein $R_4$:—$CH_2$— 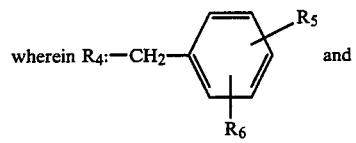 and $R_1$, $R_2$, $R_5$ and $R_6$ represent hydrogen (for $R_5$ and $R_6$ only), bromine, chlorine or alkyl with up to 5 C-atoms, $R_3$ represents hydrogen, sodium, potassium, calcium, barium or ammonium*, magnesium, bismuth, tin, zinc or copper, furthermore $R_1$, $R_2$ and $R_3$ may be interchangeably positioned in the ortho position as well as in the para position, and using fungicides.

Benzimidazole fungicides or dithiocarbamates are predominantly used preferably on potato tubers with carbendazim and thiabendazole as mixing components.

* substituted ammonium

3 Claims, No Drawings

COMPOSITIONS FOR COMBATTING PHYTOPATHOGENICAL FUNGI AND BACTERIA EMPLOYING MIXTURES OF BENZYL PHENOL DERIVATIVES AND CARBENDAZIN

BACKGROUND OF THE INVENTION AND PRIOR ART STATEMENT

This invention relates to agents comprising antimicrobially active compounds of the general formula:

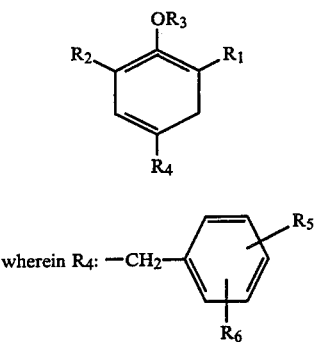

wherein $R_4$: —$CH_2$— and $R_1$, $R_2$, $R_5$ and $R_6$ represent hydrogen (for $R_5$ and $R_6$ only), chlorine, bromine or alkyl groups with up to 5 C-atoms, $R_3$ represents hydrogen, sodium, potassium, magnesium, calcium, barium, tin, zinc, copper, ammonium or substituted ammonium and wherein furthermore, $R_1$, $R_2$ and $R_4$ may be interchangeably positioned in the ortho-position as well as in the para-position, and fungicides which may be used for chemical control of phytopathogenical fungi and bacteria. These compounds are used against mycoses and bacterioses in the culture of grain, fruit, potatoes, vegetables and ornamental plants, and as a preparation and protective in storage for agricultural and horticultural crops, particularly against the inciter of the bacterial nodular-wet rot (Erwinia spp), the nodular-dry rot (Fusarium spp. and Phoma spp.) and the rhizoctonia (*Rhizoctonia solani* Kühn) on potato tubers as well as bark diseases in the culture of fruits.

Mycoses and bacterioses of culture plants cause losses of crops and losses of stored harvested goods every year, which are estimated to be more than 20 billion a year. The use of plant protectives has, in addition to cultivation, a decisive significance in the exploitation of the potentially high yield of our cultured plants and for the protection of the stored goods. For many plant diseases, no completely satisfactory or sufficiently economical solutions are known (mixed rot of stored crops, bark diseases in fruit culture and others). That relates particularly to plant protectives against bacterioses, except potato preparation. A worldwide problem is represented by the losses due to rotting of crops during storage periods, particularly potatoes. Literature of this field mentions chemical methods of fighting, which are directed against fungal and bacterial damaging inciters on the potato tubers. The benzimidazoles were among the various active compounds used that were the most effective against nodular-dry rot (Fusarium spp. and Phoma spp.) (Thiabendazol, Fuberidazol, Benomyl, Garbendazim etc.) (DD-WP No. 130,427, DD-WP No. 110,423; DE-AS Nos. 1,209,799 and 1,237,731; DE-OS No. 1,745,784; U.S. Pat. Nos. 3,631,175 and 3,657,443; DD-WP No. 107,204).

Dithiocarbamate was also used against nodular-dry rot. In order to combat rhizoctonia, principally pentachloronitrobenzene, Maneb and Mancozeb were used. In order to successfully combat bacterial nodular-wet rot (Erwinia spp.) at practical conditions, only the antibiotic chloramphenicol can be noted (DD-WP No. 78 423). In order to successfully combat all injurious inciters, it was found advantageous to use a mixture comprising a benzimidazole fungicide and chloramphenicol (DD-WP Nos. 110,423 and 130,427). This mixture forms the basis for the preferred treatment of potato tubers which are intended for subsequent storage.

The use of chloramphenicol, which was after all the first broadband antibiotic and also the first antibiotic that could be prepared synthetically, results in many risks when used as a preparation on stored crops.

WHO (WORLD HEALTH ORGANIZATION) recommends never to use paramedically an antibiotics that are used in human medicine. Therefore it is international custom not to use chloramphenicol for plant protection.

The fact that constant use of chloramphenicol as a plant protectant in agriculture causes seeping into the environment has to be taken very seriously, since it results in a reduction of sensitivity of bacteria. (Rosenthal, and others 1977). A lowered sensitivity is frequently connected to resistance factors (r-plasmids) which may be transferred by conjugation or transduction in bacteria between species, genera, families and even orders and may therefore cause disasterous consequences for remedy (WHO, 1973; RISCHE, 1975).

Antimicrobially effective compounds of the general formula I are novel active materials having the type of composition of known antimicrobially active phenols, whose synthesis may be started from a waste product of herbicide synthesis (4-chloro-2-methylphenol-synthesis) (DD-WP No. 131,746). They are characterized by good antimicrobial properties which permit their recommendation in human and in veterinary medicine. Furthermore, it is known that derivatives of phenol, such as chlorophenol, pentachlorophenol, cresol, chlorocresol, benzylphenol, benzylchlorophenol and thymol are antimicrobially active and may therefore be used as potential combination partners for fungicides for increased effectiveness and widening of the inactivity spectrum. Disadvantages of these compounds are their partially very high phytotoxicity and toxicity for warm-blooded animals, making their use in plant protection impossible.

OBJECT OF THE INVENTION

The object of the invention is the development of agents for combatting phytopathogenic fungi and bacteria which, at minimal phytotoxicity, permit a maximum fungicidal and bactericidal effect particularly against nodular-rot in stored potatoes and which are devoid of the aforementioned disadvantages, particularly when treating stored potatoes and which also open the possibility of obtaining an effect against plant diseases which thus far could not be sufficiently combatted (for instance mixed rot of stored crops, bark diseases of fruit trees etc.).

SUMMARY OF THE INVENTION

The invention is based upon the object of developing agents for combatting phytopathogenic fungi and bacteria which are preferably able to treat potato tubers which have to be stored, and which make it possible to obtain an effect against plant diseases which previously could not be sufficiently combatted. The antibiotic chloramphenicol, whose use is so frought with risk, has to be replaced by a more favorable compound, but, nevertheless the entire losses due to the rot of stored potatoes should be reduced by 60 to 90%, the yield of potato tubers should be increased by 5 to 10%, and the quality of the seeds should be obtained as well as the occurrence of plants damaged by black leg and rhizoctonia should be reduced by at least 50 percent.

Surprisingly, it was found that mixtures of antimicrobial compounds of the general formula I with a variety of fungicides, particularly with benzimidazole fungicides, allow excellent control of fungal and bacterial inciters alone or in mixed infections and furthermore show an increased effectiveness far above the effect of the single compounds. In the general formula I:

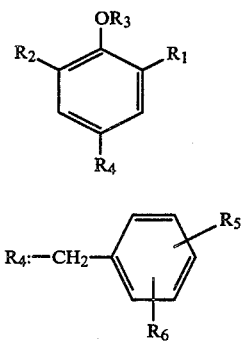

$R_1$, $R_2$, $R_5$ and $R_6$=hydrogen (only for $R_5$ and $R_6$), chlorine, bromine, alkyl-groups with up to 5 C-atoms, $R_3$=hydrogen, sodium, potassium, magnesium, calcium, barium, tin, zinc, copper, ammonium or substituted ammonium, $R_1$, $R_2$ as well as $R_4$ may furthermore be interchangeably positioned in the ortho-position as well as in the para position. The following derivatives (or their salts) are preferably used:

6-Bromo-2-methyl-4-benzylphenol,
6-Chloro-2-methyl-4-benzylphenol,
6-Bromo-2-ethyl-4-benzylphenol,
2-Chloro-6-methyl-4-benzylphenol,
2-Chloro-6-methyl-4-(4'-isopropylbenzyl)-phenol,
2-Chloro-6-ethyl-4-(4'-ethylbenzyl)-phenol,
2-Chloro-6-methyl-4-(4'-ethylbenzyl)-phenol,
6-Bromo-2-ethyl-4-(4'-isopropylbenzyl)-phenol,
6-Bromo-2-methyl-4-(4'-isopropylbenzyl)-phenol,
2-Chloro-6-methyl-4-(4'-Chlorobenzyl)-phenol,
2-Bromo-6-methyl-4-(4'-Bromobenzyl)-phenol,
2-Chloro-6-methyl-4-(4'-methylbenzyl)-phenol,
2-Chloro-6-ethyl-4-(4'-Chlorobenzyl)-phenol,
4-Chloro-2-ethyl-6-benzylphenol,
4-Chloro-2-ethyl-6-(4'-isopropylbenzyl)-phenol,
4-Chloro-2-ethyl-6-(4'-tert-butylbenzyl)-phenol,
4-Chloro-2-methyl-6-(4'-isopropylbenzyl)-phenol,
2-Chloro-6-methyl-4-(4'-tert-butylbenzyl)-phenol,
4-Bromo-2-ethyl-6-benzylphenol
2-Bromo-6-ethyl-4-(4'-Bromobenzyl)-phenol Sodium, potassium, barium, and calcium salts are preferably used.

The synergistic effect of these mixtures may be obtained when mixing ratios of the compound of the general formula I: fungicide between 100:1 and 1:100 are used for the formulations; an optimal effect is obtained when treating potato tubers to be stored with a mixing ratio of compounds of the general formula I: fungicide between 1:50 and 1:5. Various fungicides were used, such as sulfur, copper oxychloride, pentachloronitrobenzene, dithiocarbamate (zineb, maneb, mancozeb), fentin acetate, captan, captafol, propamocarb, oxathiine (carboxin, oxycarboxin), benzimidazole (benomyl, carbendazim, thiophanate-methyl, thiabendazole and fuberidazol), pyrimidine (ethirimol, dimethirimol, nuarimol and fenarimol), morpholine tridemorph, dodemorph, aldimorph and fenpropemorph), triforine, pyrazophos, triadimofon, triademenol, chloraniformethan, dichlobentrazol and metalyxyl, all of which brought greater than cumulative effects.

Benzimidazole fungicides are preferred for treatment of potato tubers against rot inciters, against bark diseases in fruit tree culture etc. The mixtures according to the invention are prepared in a form appropriate for their use with the convention carrier materials and additives. The agents according to the invention may be furthermore admixed with insecticides, bactericides, viricides drying oils, mineral substances, trace elements as well as agents for the regulation of biological processes, thereby extending their intended purpose for plant hygiene and plant care. The application of the preferably aqueous spray wash onto vegetable sprouts or for treatment of agricultural crops may be accomplished by a multitude of techniques.

DETAILED DESCRIPTION OF PREFERRED EMBODIMENTS

It was found that various types of formulation (spray powders, dust, solutions, suspensions, emulsion concentrates etc.) may be used and result in an advantageous effect. These formulations contain, according to their type, a mixture of an agent of the general formula I as well as a fungicide, one or more inert carriers (for instance kaolin, mica, bentonite sepiolite, diatomaceous earth, synthetic silica etc.) wetting-, dispersing-, or emulsifying agents (for instance ligninsulfonate, dinaphthylmethane-disulfonate, polyvinylsulfonate, alkylsuccinate, sodium sulfite, alkylbenzene sulfonate, alkylphenyl polyglycolether etc.), adhesion agents (for instance polyvinyl alcohols, vegetable or animal waxes, albumen, dextrins, gum arabic, natural and synthetic resins), solvents (for instance DMSO (dimethyl-sulfoxide), DMF (dimethylformamide), HMPT, triacetin, propylene glycol etc.), oils (mineral and triglycerides) and if so needed anti-agglomerants. Particularly for the preparation of spray powders or dust, grinding aids might be needed in addition to inert carriers, in which case substances such as chalk powder, clay, natural silicates or salts such as sodium sulfate, sodium carbonate, sodium phosphate, sodium thiosulfate and sodium bicarbonate are used.

EXAMPLES 1 TO 10

Agents formulated as spray powders have the following composition:

| AGENT I | |
|---|---|
| 4 wt. % | 2-chloro-6-methyl-4-benzylphenol |
| 50 wt. % | carbendazim |
| 40 wt. % | kaolin |
| 3 wt. % | powdered sulfite liquor |
| 3 wt. % | ethoxylated alkylphenyl polyglycol ether |
| AGENT II | |
| 5.0 wt. % | 2-chloro-6-methyl-4-benzylphenol |
| 22.5 wt. % | thiabendazole |
| 60.5 wt. % | calcium carbonte |

-continued

| | |
|---|---|
| 6 wt. % | sodium ligninsulfonate |
| 6 wt. % | ethoxylated alkylphenyl polyglycol ether |

AGENT III

| | |
|---|---|
| 4 wt. % | 2-chloro-6-methyl-4-(4'-isopropylbenzyl)-phenol |
| 50 wt. % | carbendazim |
| 6 wt. % | propylene glycol |
| 30 wt. % | synthetic silica |
| 4 wt. % | powdered sulfite liquor |
| 6 wt. % | ethoxylated alkylphenyl polyglycol ether |

AGENT IV

| | |
|---|---|
| 5 wt. % | 2-chloro-6-methyl-4-(4'-isopropylbenzyl)-phenol |
| 30 wt. % | thiabendazole |
| 5 wt. % | ethylene glycol |
| 40 wt. % | synthetic silica |
| 12 wt. % | dinapthalmethane-disulfonate |
| 3 wt. % | polyvinyl acetate |
| 5 wt. % | sodium N—oleylvinyltauride |

AGENT V

| | |
|---|---|
| 30 wt. % | 2-chloro-6-methyl-4-(4'-isopropylbenzyl)-phenol |
| 20 wt. % | metalaxyl |
| 32 wt. % | synthetic silica |
| 3 wt. % | sodium dioctylsulfosuccinate |
| 8 wt. % | hydrated sodium aluminosilicate |
| 4 wt. % | sodium ligninsulfonate |
| 3 wt. % | ethoxylated alkylphenyl polyglycol ether |

AGENT VI

| | |
|---|---|
| 30 wt. % | 2-chloro-6-ethyl-4-benzylphenol |
| 30 wt. % | maneb |
| 8 wt. % | precipitated silica |
| 25 wt. % | kaolin |
| 3 wt. % | sodium laurylsulfate |
| 4 wt. % | sodium ligninsulfonate |

AGENT VII

| | |
|---|---|
| 40 wt. % | 2-chloro-6-methyl-4-(4'-isopropylbenzyl)-phenol |
| 20 wt. % | mancozeb |
| 24 wt. % | kaolin |
| 3 wt. % | sodium dioctylsulfosuccinate |
| 6 wt. % | hydrated sodium aluminosilicate |
| 4 wt. % | sodium ligninsulfonate |
| 3 wt. % | ethoxylated alkylphenyl polyglycol ether |

AGENT VIII

| | |
|---|---|
| 40 wt. % | 2-bromo-6-methyl-4-benzylphenol |
| 20 wt. % | zineb |
| 24 wt. % | kaolin |
| 3 wt. % | sodium dioctylsulfosuccinate |
| 6 wt. % | hydrated sodium aluminosilicate |
| 4 wt. % | sodium ligninsulfonate |
| 3 wt. % | ethoxylated alkylphenyl polyglycol ether |

AGENT IX

| | |
|---|---|
| 4 wt. % | 2-bromo-6-ethyl-4-benzylphenol |
| 50 wt. % | methyl thiophanate |
| 40 wt. % | kaolin |
| 3 wt. % | powdered sulfite liquor |
| 3 wt. % | ethoxylated alkylphenyl polyglycol ether |

AGENT X

| | |
|---|---|
| 25 wt. % | 2-bromo-6-ethyl-4-benzylphenol |
| 30 wt. % | sulfur |
| 35 wt. % | diatomaceous earth |
| 5 wt. % | powdered sulfite liquor |
| 5 wt. % | ethoxylated alkylphenyl polyglycol ether |

EXAMPLES 11 TO 19

Agents according to the invention formulated as suspensions have the following compositions:

AGENT XI

| | |
|---|---|
| 30 wt. % | 2-chloro-6-methyl-4-(4'-isopropylbenzyl)-phenol |
| 3 wt. % | carbendazim |
| 19 wt. % | ethylene glycol |
| 25 wt. % | butanol |
| 3 wt. % | metaupon |
| 20 wt. % | ethoxylated alkylphenyl polyglycol ether |

AGENT XII

| | |
|---|---|
| 30 wt. % | 2-bromo-6-methyl-4-benzylphenol |
| 15 wt. % | captan |
| 34 wt. % | ethoxylated alkylphenyl polyglycol ether |
| 10 wt. % | propylene glycol |
| 4 wt. % | dibutylphthalate |
| 6 wt. % | triacetin |
| 1 wt. % | antaphron NE 30 |

AGENT XIII

| | |
|---|---|
| 10 wt. % | 2-bromo-6-methyl-4-benzylphenol |
| 5 wt. % | Cu—stearate |
| 10 wt. % | dimethylamino ethanol |
| 20 wt. % | DMSO |
| 20 wt. % | methylboxalin |
| 35 wt. % | ethoxylated alkylphenyl polyglycol ether |

AGENT XIV

| | |
|---|---|
| 5 wt. % | 2-bromo-6-methyl-4-benzylphenol |
| 5 wt. % | sulfur |
| 10 wt. % | dimethylamino ethanol |
| 25 wt. % | DMSO |
| 25 wt. % | xylol |
| 30 wt. % | ethoxylated alkylphenyl polyglycol ether |

AGENT XV

| | |
|---|---|
| 10 wt. % | 2-bromo-6-methyl-4-benzylphenol |
| 5 wt. % | griseofulvin |
| 25 wt. % | dimethylamino ethanol |
| 30 wt. % | DMSO |
| 30 wt. % | ethoxylated alkylphenyl polyglycol ether |

AGENT XVI

| | |
|---|---|
| 12 wt. % | 2-bromo-6-methyl-4-benzylphenol |
| 15 wt. % | copper oxychloride |
| 15 wt. % | synthetic silica |
| 6 wt. % | propylene glycol |
| 2 wt. % | hydroxymethylcellulose |
| 5 wt. % | ethoxylated alkylphenyl polyglycol ether |
| 45 wt. % | water |

AGENT XVII

| | |
|---|---|
| 5 wt. % | 2-chloro-6-ethyl-4-benzylphenol |
| 5 wt. % | sulfur |
| 10 wt. % | synthetic silica |
| 50 wt. % | spindle oil |
| 30 wt. % | ethoxylated alkylphenyl polyglycol ether |

AGENT XVIII

| | |
|---|---|
| 25 wt. % | 6-bromo-2-methyl-4-benzylphenol |
| 25 wt. % | tridemorph |
| 16 wt. % | propylene glycol |
| 34 wt. % | ethoxylated alkylphenyl polyglycol ether |

AGENT XIX

| | |
|---|---|
| 20 wt. % | 6-bromo-2-methyl-4-benzylphenol |
| 20 wt. % | metalaxyl |
| 30 wt. % | propylene glycol |
| 10 wt. % | DMSO |
| 20 wt. % | ethoxylated alkylphenyl polyglycol ether |

EXAMPLE 20

Test on potato tubers in the laboratory

The following agents according to the invention are used: III, XX, XXI (2-chloro-6-methyl-4-benzylphenyl+carbendazim are mixed for use at a ratio of 1:50 and 1:12.5 respectively and formulated corresponding to agent III), agent II, thiabendazole and carbendazim.

The formulations and the comparison agents carbendazim are thiabendazole are studied in laboratory tests against Fusarium-dry rot (Fusarium spp.), bacterial wet rot (Erwinia spp.) and mixed rot (Fusarium spp.+Erwinia spp.) on potato tubers of the Adretta variety, after artificial infections. The fungicidal efficiency of the tested agents is shown in table 1. The fungicidal efficiency was calculated from the degree of infection. Agent III according to the invention is distinctly superior in its fungicidal efficiency against the three rot-types over the individual substances. The excellent effect against bacterial wet rot and mixed rot is prominent here, considering that these diseases are very difficult to combat.

TABLE 1

Fungicidal effect of agents according to the invention II, III, XX, and XXI compared with 2-chloro-6-methyl-4-(4'-isopropylbenzyl)-phenol, 2-chloro-6-methyl-4-benzyl-phenol, thiabendazole and carbendazim against Fusarium-dry rot (Fusarium spp.), bacterial wet rot (Erwinia spp.) and mixed rot (fusarium spp. + Erwinia spp.) on potato tubers of the "Adretta" variety, after artificial infection at laboratory conditions.

| Variant | amount of agent per ton | Degree of efficiency in % | | |
|---|---|---|---|---|
| | | Fusarium dry rot | wet rot | mixed rot |
| 2-chloro-6-methyl-4-(4-isopropybenzyl)-phenol + carbendazim (agent III) | 10 g + 125 g | 90 | 100 | 100 |
| 2-chloro-6-methyl-4-benzylphenol + thiabendazole (agent II) | 10 g + 45 g | — | — | 99 |
| 2-chloro-6-methyl-4-(4'-isopropylbenzyl)-phenol | 10 g | 30 | 40 | 10 |
| 2-chloro-6-methyl-4-benzylphenol + carbendazim (agent XX) | 2.5 g + 125 g | 83 | 100 | 95 |
| 2-chloro-6-methyl-4-benzylphenol + carbendazim (agent XXI) | 10 g + 125 g | 92 | 100 | 98 |
| 2-chloro-6-methyl-4-benzylphenol | 2.5 g | 28 | — | 7 |
| 2-chloro-6-methyl-4-benzylphenol | 10 g | 37 | 40 | 10 |
| carbendazim | 125 g | 70 | 10 | 10 |
| thiabendazole | 45 g | — | — | 72 |

EXAMPLE 21

Test on potato tubers at practical conditions (of the "Libelle" variety)

Potato tubers of the "Libelle" variety serve to test the mixtures according to the invention (agent XX and XXI) at storage under practical conditions. Additionally, a mixture according to the invention (agent XXII) 2-chloro-6-methyl-4-benzylphenol:Carbendazim 1:10 was formulated with the conventional formulation adjuvants (corresponding to agent III) and included in the tests. 5 kg samples (5 repetitions in a laboratory preparation drum) were additionally infected, treated and stored in a conventional manner. Bercema-Demex, a conventional preparation containing chloramphenicol as the bactericidal component, was used for comparison. The effect of the agents is shown in Table 2, separate in respect to Fusarium-dry rot, bacterial wet rot and mixed rot. In their fungicidal effect, the agents according to the invention are as good as the comparative agent Bercema-Demex which contains chloramphenicol. One of the agents according to the invention shows even a better effect against mixed rot.

TABLE 2

Fungicidal effect of agents according to the invention compared to the conventional agent Bercema-Demex, against Fusarium-dry rot (Fusarium spp.), bacterial wet rot (Erwinia spp.) and mixed rot (Fusarium spp. + Erwinia spp.) on potato tubers of the "Libelle" variety after additional infection under practical conditions.

| Variant | amount used per ton | Infection under Practical Conditions rot infection (in %) | | | |
|---|---|---|---|---|---|
| | | Fusarium dry rot | wet rot | mixed rot | sum of rots |
| untreated control | — | 10.3 | 0 | 5.7 | 16.0 |
| 2-chloro-6-methyl-4-benzylphenol + carbendazim (agent XX) | 2.5 g + 125 g | 6.5 | 0 | 0.8 | 7.3 |
| 2-chloro-6-methyl-4-benzylphenol + carbendazim (agent XXI) | 10 g + 125 g | 7.1 | 0 | 0.9 | 8.0 |
| 2-chloro-6-methyl-4-benzylphenol + carbendazim (agent XXII) | 24 g + 125 g + | 6.0 | 0 | 0.4 | 6.4 |
| carbendazim + chloroamphenicol (Bercema-Demex) | 115 g + 2.6 g | 6.4 | 0 | 0.8 | 7.2 |

EXAMPLE 22

Testing of mixtures according to the invention against grain mildew (*Erysiphe graminis* DC)

The mixtures according to the invention (agents XI, XIII, XV) are used for the experiments. For the execution of the test, wheat plants in their one-leaf state were infected with *Erisyphe graminis* DC f. sp. *triticai Marchal* and treated after 24 hours with the chosen agent to dripping wetness. The degree of fungicidal effect was calculated from yield classifications. The mixtures according to the invention show very good fungicidal effect against wheat mildew under laboratory conditions.

| Variant | concentration of agent (in ppm) | degree of effect (in %) |
|---|---|---|
| 2-chloro-6-methyl-4-(4'-isopropylbenzyl)-phenol + carbendazim (agent XI) | 750 | 100 |
| 2-bromo-6-methyl-4-benzylphenol + Cu—stearate (agent XIII) | 300 + 150 | 95 |
| 2-bromo-6-methyl-4-benzylphenol + griseofulvin (agent XV) | 300 + 150 | 100 |

EXAMPLE 23

Testing of mixtures according to the invention against Botrytis spp. on tulips

Tulip bulbs infected with Botrytis spp. are treated with mixtures according to the invention (agents XI and XII) by immersion in an aqueous bath. These tulip bulbs were planted in the fall and inspected the following year for symtoms of disease caused by Botrytis spp. The result of these tests are displayed in Table 4. It was found that the mixture according to the invention resulted in an excellent controlling effect.

TABLE 4

Fungicidal effect of mixtures according to the invention against Botrytis spp. on tulip bulbs

| Variant | concentration of application % | degree of effect % |
|---|---|---|
| 2-chloro-6-methyl-4-(4'-isopropylbenzyl)-phenol + carbendazim (agent XI) | 0.15 + 0.05 | 98 |
| 2-bromo-6-methyl-4-benzylphenol + captan (agent XII) | 1.00 + 0.05 | 92 |

EXAMPLE 24

Testing of mixtures according to the invention (agents VII, VIII, and XIV) against *Phytophthora infestans*

Tomato leaves were treated with the mixtures according to the invention until dripping wet and were infected consecutively with *Phytophthora infestans*. The fungicidal effect of the test agents is displayed in Table 5. The degree of fungicidal effect was calculated by counting the infected spots against the degree of infection. As can be observed from the test results, the mixtures according to the invention possess an excellent fungicidal effect. It is expected that by mixing—according to the invention—with metalaxyl, the danger of production of resistance against the agent metalaxyl can be reduced or prevented, due to combination with an antimicrobial compound of the general formula I.

| Variants | concentration of agent (ppm) | degree of effect (%) |
|---|---|---|
| 2-chloro-6-methyl-4-(4'-isopropylbenzyl)-phenol + mancozeb (agent VII) | 150 | 92 |
| 2-bromo-6-methyl-4-benzylphenol + zineb (agent VIII) | 150 | 80 |
| 2-bromo-6-methyl-4-benzylphenol + metalaxyl (agent XIV) | 150 | 93 |

EXAMPLE 25

Testing against bark disease inciter of fruit in a Petri dish

A mixture according to the invention is prepared by mixing 2-chloro-6-methyl-4-benzylphenol with the benzimidazole fungicide carbendazim at a ratio of 50:1 and by formulating it with the conventional formulation adjuvants. The mixture according to the invention or 2-chloro-6-methyl-4-benzylphenol or carbendazim respectively were added to nutritional agar for fungi and transferred into Petri dishes.

In order to study the effects of the test, various inciters of bark disease of fruit trees were inoculated (Nectria spp., Pezicula spp., Gloeosporium spp.). Evaluation was performed by measuring the growth of the mycelium and is expressed as a degree of fungicidal effect. The results of the test may be found in Table 6. The agent according to the invention has a fungicidal effect against the inciters of bark diseases distinctly superior to the effect of the individual substances.

TABLE 6

Fungicidal effect of the agent according to the invention compared with 2-chloro-6-methyl-4-benzylphneol and carbendazim against inciters of bark diseases of fruit trees, found on the Petri dish test

| Inciter | Variant | Concentration of use or agent in ppm. | degree of effect (%) |
|---|---|---|---|
| Nectria spp. | 2-chloro-6-methyl-4-benzylphenol + carbendazim | 300 | 100 |
| | 2-chloro-6-methyl-4-benzylphenol | 300 | 30 |
| | Carbendazim | 1 | 60 |
| Pezicula spp. | 2-chloro-6-methyl-4-benzylphenol + carbendazim | 300 | 100 |
| | 2-chloro-6-methyl-4-benzylphenol | 300 | 30 |
| | Carbendazim | 1 | 45 |
| Gloeosporium spp. | 2-chloro-6-methyl-4-benzylphenol + carbendazim | 300 | 100 |
| | 2-chloro-6-methyl-4-benzylphenol | 300 | 25 |
| | Carbendazim | 1 | 40 |

EXAMPLE 26

Treatment against wheat bunt (Tilletia spp.)

For these tests, two mixtures according to the invention were prepared, comprising 2-chloro-6-methyl-4-benzylphenol and carbendazim with the conventional formulation adjuvants at ratios 10:1 and 5:1, and were tested according to the Gassner method. The fungicidal effect of the tested agent is determined by treating wheat seeds (of the "Alcedo" variety), artificially contaminated with Tilletia spores, and incubating in sludge soil. The formation of sporidia was used as a criteria for evaluation. Table 7 displays the results of testing the mixtures according to the invention compared with a conventional preparation (Falisan-Universal-Trockenbeize 69). The antimicrobial agent successfully prevents the formation of sporidia. It is, though, surpassed by the mixture according to the invention. The effect of the control preparation was approached only by an agent according to the invention.

TABLE 7

Results of treatment against wheat bunt (Tilletia spp.)

| Agent | agent used per 100 Kg seed | inhibition of sporidia formation basic number |
|---|---|---|
| untreated control | — | 1 |
| 2-chloro-6-methyl-benzylphenol + carbendazim | 20 g + 2 g | 3 |
| 2-chloro-6-methyl-4-benzylphenol + carbendazim | 10 g + 2 g | 2 |
| 2-chloro-6-methyl-4-benzylphenol | 20 g | 2 |
| 2-chloro-6-methyl-4-benzylphenol | 10 g | 2 |
| phenyl-mercury-silver-acetate (Falisan-Universal-Trockenbeize 69) | 4.88 g | 3 | legend: basic number
0 = sporidia formation above 60%
1 = sporidia formation 15 to 60%
2 = sporidia formation 3 to 15%
3 = sporidia formation 0 to 3%

We claim:

1. A mixture for controlling phytopathogenic fungi and bacteria, comprising 2-chloro-6-methyl-4-benzylphenol and carbendazim in a weight proportion in the range of 1:50 to 1:5.

2. A mixture according to claim 1, further comprising ethoxylated alkylphenyl polyglycol ether.

3. A mixture according to claim 2, consisting of
4 wt. % 2-chloro-6-methyl-4-benzylphenol;
50 wt. % carbendazim;
40 wt. % kaolin;
3 wt. % powdered sulfite liquor; and
3 wt. % ethoxylated alkylphenyl polyglycol ether.

* * * * *